US005989877A

United States Patent [19]

De Pater et al.

[11] Patent Number: 5,989,877

[45] Date of Patent: Nov. 23, 1999

[54] SELECTIVE PROCESS FOR THE DEACYLATION OF ACYLATED COMPOUNDS

[75] Inventors: Robertus M. De Pater, Delft; Mieke Sibeyn, Amersfoort, both of Netherlands

[73] Assignee: Gist-Brocades B.V., Netherlands

[21] Appl. No.: 08/817,805

[22] PCT Filed: Aug. 5, 1996

[86] PCT No.: PCT/EP96/03495

§ 371 Date: Apr. 23, 1997

§ 102(e) Date: Apr. 23, 1997

[87] PCT Pub. No.: WO97/06204

PCT Pub. Date: Feb. 20, 1997

[30] Foreign Application Priority Data

Aug. 3, 1995 [EP] European Pat. Off. .............. 95202125

[51] Int. Cl.[6] ................................ C12P 7/18; C12P 1/04; C07D 309/30; C07C 67/02

[52] U.S. Cl. .......................... 435/158; 435/170; 549/292; 560/256

[58] Field of Search .................................... 435/158, 170, 435/171, 252.1, 254.1, 254.3; 549/292; 560/119, 256

[56] References Cited

U.S. PATENT DOCUMENTS 5,451,688 9/1995 Kogen et al. ........................... 549/292

*Primary Examiner*—Jean C. Witz
*Assistant Examiner*—Susan Hanley
*Attorney, Agent, or Firm*—Bierman, Musierlian and Lucas

[57] ABSTRACT

The invention provides a simple and selective method for the deacylation of 4-acylated statins during the preparation of statins from a fermentation broth, more specifically a reduction of impurities from the process, by increasing the pH of the fermentation broth.

3 Claims, 2 Drawing Sheets

SELECTIVE PROCESS FOR THE DEACYLATION OF ACYLATED COMPOUNDS

This application is the National Stage of International Application No. PCT/EP96/03495, filed Aug. 5, 1996.

FIELD AND BACKGROUND OF THE INVENTION

The present invention provides an improvement for the recovery of lovastatin, compactin or pravastatin from fermentation broths.

Lovastatin for instance is produced as a secondary metabolite by various microorganisms such as *Aspergillus terreus* (U.S. Pat. No. 4,231,938) or *Monascus ruber* (U.S. Pat. No. 4,323,648). During the fermentation also lovastatin related byproducts such as 4-acetyl lovastatin are produced.

Lovastatin, usually in the acid form, can be isolated from the fermentation broth in different ways. The first stage is formed by purification yielding crude crystals. These crude crystals still comprise related compounds like 4-acetyl lovastatin. As lovastatin is a pharmaceutical compound that has to meet high purity requirements, additional purification in order to remove the lovastatin related impurities is necessary. The lovastatin-related impurities are generally removed by multiple recrystallizations, by column chromatography as described in U.S. Pat. No. 4,231,938 or preparative HPLC (WO 92/16276), decreasing the yield significantly.

BRIEF DESCRIPTION OF THE INVENTION

By the process of the present invention impurities present in the broth filtrate are removed, thus preventing the need for their removal via additional recrystallizations and resulting in an increased yield.

During the application of the process of the present invention to a broth filtrate of a microorganism producing statins as for instance *Aspergillus terreus*, surprisingly 4-acetyl lovastatin is selectively converted into lovastatin instead of being converted into dehydro lovastatin via dehydration which occurs for pure 4-acetyl lovastatin (see FIG. I). Another surprising fact is that the 2-methyl butanoate group is not removed during the application of the invention.

The process of the present invention has neither been described nor suggested in the prior art.

BRIEF DESCRIPTION OF THE FIGURES

FIG. I. Reaction scheme of the deacylation of 4-acetyl lovastatinic acid to lovastatinic acid (a) and the dehydratation of 4-acetyl lovastatinic acid to dehydro lovastatinic acid (b)

FIG. II. Thin layer chromatogram (TLC) showing reduction of impurities in crude lovastatin crystals after applying the process of the invention. Eluent: chloroform/methanol=9/1; detection: iodine staining; run product: 2 $\mu$l of a solution, consisting of crude lovastatin crystal in toluene, concentration 50 g/l.

Figure 1:
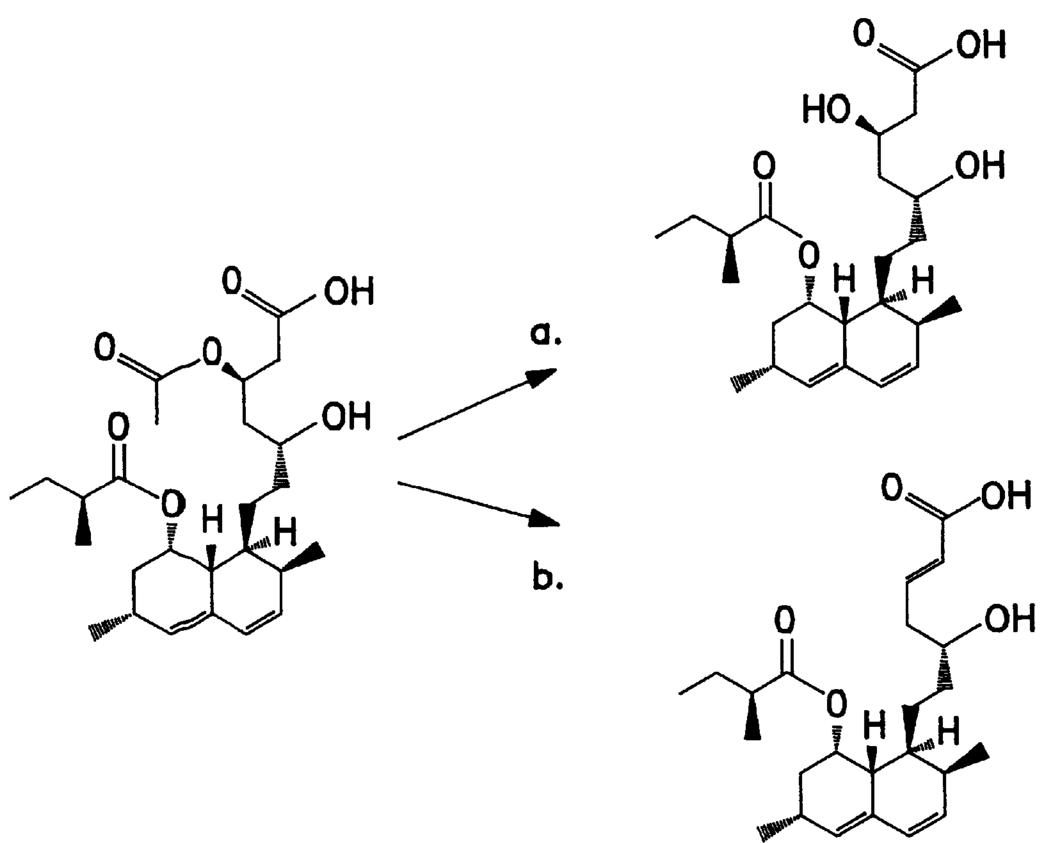
Figure 2:
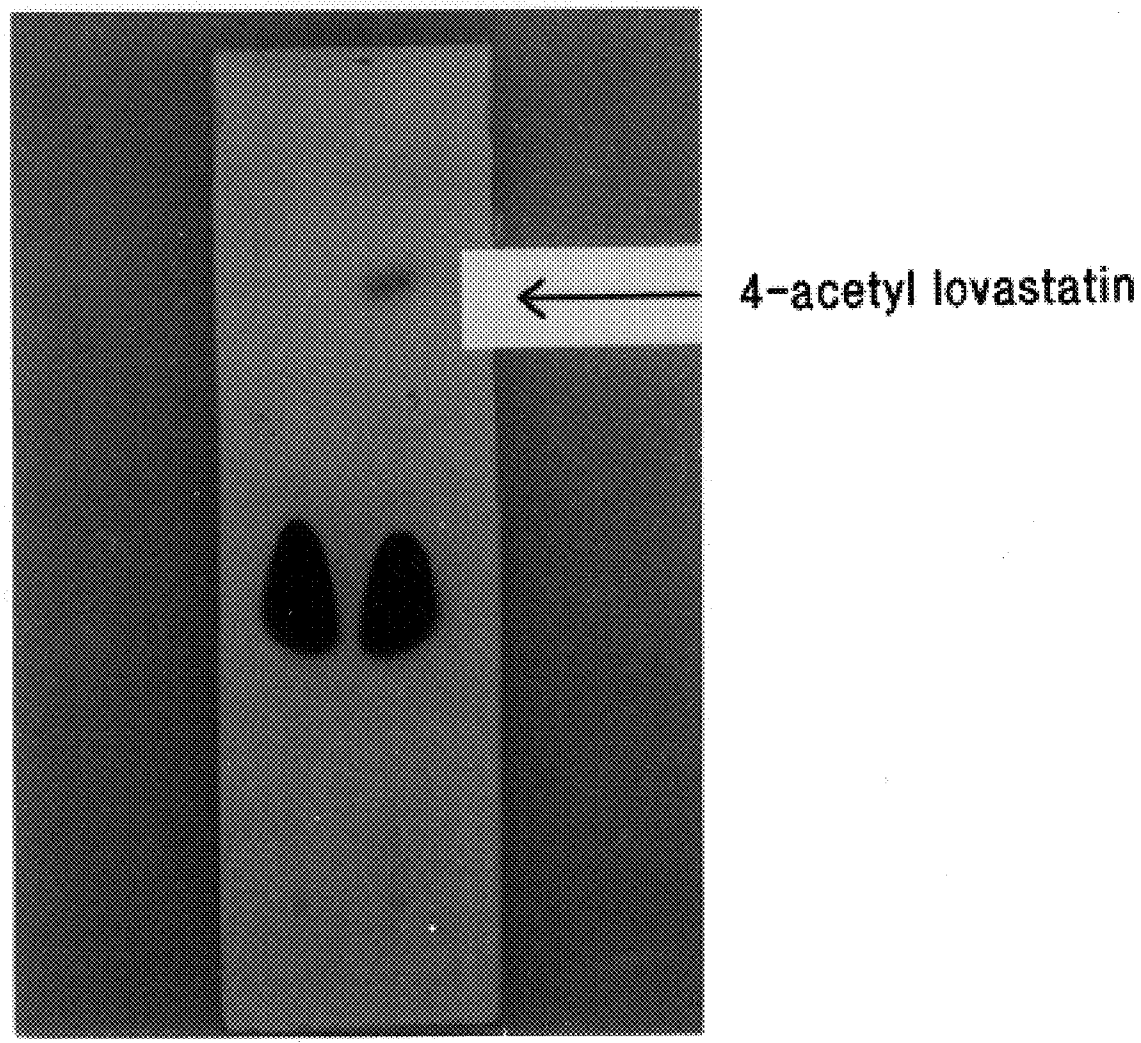

Right side: crude crystal from untreated broth filtrate; left side: crude crystal from broth filtrate which has been stirred for 2 hours at 50° C. and pH 12.5.

DETAILED DESCRIPTION OF THE INVENTION

The present invention concerns a process to improve the recovery of lovastatin, pravastatin or compactin from a broth filtrate. This process comprises:

growing in a medium microorganisms that produce a member of the group consisting of lovastatin, compactin or pravastatin resulting in a product medium removal of the biomass from the product medium to obtain a clarified broth filtrate isolating the purified lovastatin, compactin or pravastatin, respectively, characterized by adjusting the pH of the clarified broth filtrate above about pH 10. Preferably, said method also comprises heating the clarified broth filtrate above approximately 50° C.

The process of the present invention offers a simple and selective method of the deacylation of 4-acylated statins in broth filtrates, resulting in an improved yield and purity of the crystals. During the treatment at high pH the 4-acylated statin is converted into the related statin. The conversion rate of, for instance, 4-acetyl lovastatin into lovastatin in broth filtrate is dependent on the pH and the reaction temperature. In a preferred embodiment of the present invention, the treatment is carried out at pH-values above pH=10, more preferably between pH=10 and pH=13, most preferably between pH=11 and pH=12.5. Also temperatures between 60° C. and 95° C. are preferred. By applying higher pH-values and/or higher temperatures the reaction time for complete deacylation decreases.

The process of increasing the pH can be advantageously be applied to filtrates of fermentation broths from any microorganism that is capable of producing a member of the group consisting of lovastatin, pravastatin or compactin. Microorganisms capable of producing statins may be one of the following species:

Penicillium, Hypomyces, Paecilomyces, Eupenicillium, Trichoderma, Aspergillus, Monascus, Phoma, Doratomyces, Gymnoascus or Pleurotus.

The fermentation of these microorganisms in order to produce statins is carried out in aqueous media similar to those employed for the production of other fermentation products. Such media contain sources of carbon, nitrogen and inorganic salts assimilable by the microorganism.

In general, carbohydrates such as sugars, for example glucose, maltose, sucrose, xylose, mannitol and the like and starches such as grains, for example, oats, ryes, cornstarch, corn meal and the like can be used either alone or in combination as sources of assimilable carbon in the nutrient medium. These carbon sources can be used individually, or several such carbon sources may be combined in the medium.

In general, many proteinaceous materials may be used as nitrogen sources in the fermentation process. Suitable nitrogen sources include for example, yeast hydrolysates, primary yeast, yeast extracts, soybean meal, cottonseed flour, hydrolysates of casein, corn steep liquor, distiller's solubles or tomato paste and the like. The sources of nitrogen can be used either alone or in combination.

Among the nutrient inorganic salts which can be incorporated in the culture media are the customary salts capable of yielding sodium, potassium, ammonium, calcium, phosphate, sulfate, chloride, carbonate and like ions. Also included are trace metals such as cobalt, manganese, iron and magnesium.

It should be noted that the media described in the Examples are merely illustrative of the wide variety of media which may be employed, and yet are not intended to be limitative. Specifically, the carbon sources used in the culture media to produce lovastatin included dextrose, dextrin, glucose, sucrose, oat flour, oatmeal, molasses, citrate, acetate, soybean oil, glycerol, malt extract, cod liver oil, starch, ethanol, figs, ascorbate, and lard oil. Included as nitrogen sources were peptonized milk, autolyzed yeast, yeast extract, yeast RNA, tomato paste, casein, primary yeast, peanut meal, distillers solubles, corn steep liquor, soybean meal, corn meal, NZ amine, beef extract, asparagine, cottonseed meal, ammonia and ammonium sulphate. The major ionic components, $CaCO_3$, $KH_2PO_4$, $MgSO_4.7H_2O$ and NaCl can also be added as well as small amounts of $CoCl_2.6H_2O$ and traces of Fe, Mn, Mo, B and Cu. The nutrients can either be dosed in the batch medium or can be (partly) fed during the fermentation.

The process of the present invention is applied directly to the broth after removal of the biomass, prior to further purification steps. For instance, an aqueous solution of earth alkalihydroxide or ammoniumhydroxide can be conveniently used for such a reaction. The broth filtrate is treated at high pH and preferably at high temperatures. Furthermore, during this treatment at high pH, proteins present in the fermentation broth filtrate are denaturated, facilitating their removal from the product in the subsequent reaction steps. Further purification steps may comprise extraction, adsorption to a hydrophobic resin, ionexchange, column chromatography etc.

The following examples will illustrate the invention and are offered by way of illustration and not by way of limitation. Experiments II to IV are carried out under a nitrogen atmosphere.

EXAMPLES

Example I

Production of Lovastatin by Means of Fermentation of *Aspergillus terreus* Strain AD43

*Aspergillus terreus* strain AD43, DS number 28373 has been deposited with the Centraal Bureau voor Schimmelcultures (CBS, Delft, The Netherlands), and has been granted CBS accession number CBS 456.95.

One 1 ml vial of a spore suspension of *Aspergillus terreus* strain AD43, stored in glycerol at −80° C. was opened aseptically, and contents were suspended in a 2 liter shake flask containing 500 ml of the following medium (heated in an autoclave for 20 minutes at 121° C.):

| Ingredient | Amount per kg |
|---|---|
| Glucose.I $H_2O$ | 10 g |
| Oatmeal | 10 g |
| Tomato paste | 40 g |
| Corn steep solids | 5 g |
| Trace elements | 1 g |

Composition of the trace element solution (per 100 ml of distilled water): $FeSO_4.7H_2O$, 1 g; $MnSO_4.1H_2O$, 1 g; $CuCl_2.2H_2O$, 0.025 g; $CaCl_2.2H_2O$, 0.1 g; $H_3BO_4$, 0.056 g; $(NH_4)_6Mo_7O_{24}.4H_2O$, 0.019 g; $ZnSO_4.7H_2O$, 0.2 g.

The shake flask was incubated at 28° C. during 24 hours in a rotary shaker at 280 rpm (throw of 3.5 cm). 20 ml of the shake flask broth (diluted in 100 ml of saline solution) was then inoculated into a fermenter with 10 kg of broth weight. The composition of the fermentation broth was as follows:

| Ingredient | Amount per kg |
|---|---|
| Glucose.1$H_2O$ | 20 g |
| Yeast extract paste | 33 g |
| Polypropylene glycol 2000 | 2.5 ml |

Glucose and the yeast extract/polypropylene glycol solution were sterilized separately (20 minutes at 121° C.).

Fermentation conditions were as follows:

pH was kept constant at 6.5, using $H_2SO_4$ and NaOH

Temperature was 28° C.

Air supply was 1 vvm

As soon as all glucose was consumed a glucose/yeast extract feed was started at a rate of 1.2 g of glucose per kg of broth per hour. Composition of the feed:

| Ingredient | Amount per kg |
|---|---|
| Glucose.1 $H_2O$ | 500 g |
| Yeast extract paste | 17 g |
| Polypropylene glycol 2000 | 14 ml |

After 192 hours of fermentation the pH of the broth was raised to pH 10 with NaOH and the broth was diluted with 4 liters of water.

This fermentation yielded 385 mg of lovastatin acid per liter of fermentation broth before dilution. After dilution a lovastatin acid content of 411 mg/l was measured.

Example II

Effect of Heat Treatment of Broth Filtrate on the Purity of Lovastatin Crystals 1,000 ml of broth filtrate of strain AD43 (lovastatin acid concentration 0.4 g/l, produced according to example I) was brought to pH 12.5 with 2 N NaOH at 25° C., and subsequently brought to 50° C. for 2 hrs. After 2 hrs, the reaction was completed, and the reaction mixture was cooled to room temperature. Then the pH was lowered to pH 4 using sulfuric acid, 3,000 ml of toluene were added en mixed during 30 minutes.

The toluene layer was separated from the water layer, and subsequently concentrated to a volume of 80 ml by evaporation at 40° C. under vacuum.

The lovastatin acid in the extract was converted into the lactone by heating it to 90° C. for 3 hours (yield of conversion was 99.2%). After cooling to room temperature, the toluene was mixed with 80 ml of water, while the pH was adjusted to pH=10 with NaOH. After separation of the layers, the toluene layer was mixed again with 80 ml of fresh water, while the pH was adjusted to pH=4 with sulfuric acid. After separation of the layers, the toluene layer was treated with 0.1 g of active coal, Norit SX ultra. Subsequently the toluene solution was filtrated and further concentrated to 15 ml by evaporation. Cooling to −10° C. resulted in crystallization. The crystals were washed with 5 ml of cold toluene, and dried under vacuum at room temperature. In these crystals no 4-acetyl lovastatin could be detected, neither by TLC nor by proton NMR.

In contrast, crystals obtained from the fermentation broth via the process described above but without a heat treatment of the broth filtrate at pH 12, did contain 4-acetyl lovastatin as detected by TLC (see FIG. II). Also proton NMR-analysis showed the presence of 1.1% of 4-acetyl lovastatin in these crystals.

Example III

Comparison of Various Heat Treatment Conditions of Broth Filtrate on the Purity of Lovastatin Crystals Various portions of broth filtrate were treated at different pH-values and temperatures and of different duration, as shown in Table 1. For each set of parameters, 1,000 ml of a broth filtrate of strain AD43 (lovastatin acid concentration of 0.4 g/l) was used. After the treatment, the filtrate was brought to pH=4 using sulfuric acid, and 1,000 ml of toluene were mixed with the filtrate for 30 minutes. The layers were subsequently separated, and the toluene layer was concentrated to a volume of 80 ml by evaporation, and kept at 90° C. for 3 hours. After cooling to room temperature, the toluene was mixed with 40 ml of water, while the pH was adjusted to pH=10 with NaOH. After separation of the layers, the toluene was mixed with another 40 ml of water, while the pH was adjusted to pH=4 using sulfuric acid. After separation of the layers, 0.1 g of active coal, Norit SX Ultra, was added to the toluene solution. The toluene solution was filtered in order to remove the active coal, and subsequently concentrated to 15 ml by evaporation. Cooling to −10° C. resulted in crystallization. The crystals were filtered, washed with 5 ml of cold toluene and then dried under vacuum at room temperature. The crystals were analyzed qualitatively by TLC (Merck silicagel 60F, d=0..25 mm, art.nr. 5715; mobile phase chloroform/methanol in a ratio of 30/1), detection by UV at 254 nm (sensitivity is 0.3% at 0.1 mg of run product) and by iodine staining (sensitivity 0.1% at 0.1 mg of run product). Results of these treatments are shown in Table I.

TABLE 1

Effect of various heat treatment parameters on the purity of lovastatin crystals. Qualitative analysis by TLC with UV-detection (sensitivity 0.3% for 0.1 mg of run product) and iodine staining (sensitivity 0.1% for 0.1 mg of run product)

| pH | Temperature/ ° C. | Time/ minutes | 4-acetyl lovastatin in crystal UV* | iodine* |
|---|---|---|---|---|
| 10 | 21 | 30 | + | + |
| 10 | 60 | 30 | + | + |
| 10 | 90 | 10 | + | + |
| 11 | 90 | 10 | − | − |
| 11 | 90 | 5 | − | ○ |
| 12 | 21 | 90 | − | + |
| 12 | 60 | 30 | − | − |
| 12 | 60 | 10 | − | ○ |
| 12 | 90 | 10 | − | − |
| 12 | 90 | 5 | − | ○ |

− not detectable
○ weak spot
+ detectable

Example IV

Reaction of the Pure Compound 4-Acetyl Lovastatin Upon Heat Treatment in Aqueous Solution at High pH (a) Preparation of 4-Acetyl Lovastatin Acetic anhydride (7 ml; 0.073 mol) was added in one shot to pure lovastatin (25 g; 0.062 mol) and 4-dimethylamino pyridine (1.53 g; 0.013 mol, 20%) in dry pyridine (120 mL at 0° C.) under nitrogen. The mixture was stirred at 0° C. for 6 hours. By TLC-analysis (see Example 3 for description of the method) of the reaction mixture it was shown that all lovastatin has disappeared, presumably converted into 4-acetyl lovastatin.

Subsequently the pyridine was removed by evaporation and ethyl acetate was added (240 mL) The solution was washed with 240 mL of a saturated solution of NaCl. The layers were separated, and the organic layer was dried over anhydrous magnesium sulfate. The organic layer was filtered and subsequently ethyl acetate was evaporated, yielding a light yellow oil. This oil was identified as a 1/1 mixture of 4-acetyl lovastatin and dehydro lovastatin by proton NMR.

The 4-acetyl lovastatin appeared to be unstable upon storage under $N_2$ and further conversion of 4-acetyl lovastatin to dehydro lovastatin occurred.

(b) Purification of 4-Acetyl Lovastatin by Chromatography 3 g of a ½ mixture of 4-acetyl lovastatin and dehydro lovastatin were dissolved in 2 ml of chloroform/methanol (40/1). Subsequently the solution was absorbed onto 120 g of silicagel (Baker 533), which in turn was developed under pressure (0.3 bar) with a mixture of chloroform/methanol (ratio 40/1). Four fractions were collected of which the solvent was removed by evaporation. The third fraction contained 4-acetyl lovastatin with a trace of dehydro lovastatin (0.28 g), and the fourth contained only 4-acetyl lovastatin (0.3 g).

(c) Reaction of 4-Acetyl Lovastatin in an Aqueous Solution at High pH and Elevated Temperature 0.3 g of 4-acetyl lovastatin (fourth fraction of Example IV b) was dissolved in a mixture of 2 mL of N,N-dimethylformamide (DMF, Merck) and 98 mL of demineralized water. The pH was adjusted to pH 12.5 with NaOH, and the solution was stirred at 60° C. for 1 hour.

Subsequently the reaction mixture was cooled to room temperature, then the pH was adjusted to pH=4 with sulfuric acid and 60 mL of toluene were mixed with the aqueous solution for 0.5 hour in order to extract the reaction products.

After separation of the layers, the toluene solution was heated at 90° C. for 6 hours. The toluene was then removed by evaporation, yielding a small amount of product. This product was identified by proton NMR as predominantly dehydro lovastatin, while it did not contain any lovastatin.

We claim:

1. A method of improving the purity of a compound selected from the group consisting of lovastatin, pravastatin and compactin from a broth filtrate comprising the steps of:

a. culturing microorganisms capable of making said compound in a medium to produce a biomass and said compound, b. removing said biomass from said medium to obtain a clarified broth filtrate, c. treating the broth filtrate under parameters of pH, temperature and time selected from the group consisting of a pH of 11 and a temperature of 90° C. for 10 minutes, a pH of 12 and a temperature of 60° C. for 30 minutes and a pH of 12 and a temperature of 90° C. for 10 minutes; and d. recovering said compound from said broth filtrate.

2. A process to improve the purity of a member selected from the group consisting of lovastatin, pravastatin and compactin from a broth filtrate, comprising culturing in a medium microorganisms that produce a member selected from the group consisting of lovastatin, compactin and pravastatin and undissolved biomass, removal of the biomass from the product medium to obtain a clarified broth filtrate, adjusting the pH of the clarified broth filtrate between pH=11 and pH=12.5 at a temperature between 50° C. and 90° C., optionally lactonization of the acid formed by heating or acidifying or a combination thereof in a solvent and isolating the purified lovastatin, compactin or pravastin, respectively.

3. A process according to claim 2, wherein the temperature is between 60 and 90° C.

* * * * *